(12) United States Patent
Fulbrook

(10) Patent No.: US 11,517,634 B2
(45) Date of Patent: Dec. 6, 2022

(54) FIELD OF REACH ULTRAVIOLET LIGHT DISINFECTING SYSTEM

(71) Applicant: Jim E. Fulbrook, Fairfax, VA (US)

(72) Inventor: Jim E. Fulbrook, Fairfax, VA (US)

(*) Notice: Subject to any disclaimer, the term of this patent is extended or adjusted under 35 U.S.C. 154(b) by 0 days.

(21) Appl. No.: 17/441,843

(22) PCT Filed: May 6, 2021

(86) PCT No.: PCT/US2021/031126
§ 371 (c)(1),
(2) Date: Sep. 22, 2021

(87) PCT Pub. No.: WO2021/226357
PCT Pub. Date: Nov. 11, 2021

(65) Prior Publication Data
US 2022/0313847 A1    Oct. 6, 2022

Related U.S. Application Data

(60) Provisional application No. 63/020,936, filed on May 6, 2020.

(51) Int. Cl.
*A61L 2/00* (2006.01)
(52) U.S. Cl.
CPC ......... *A61L 2/0047* (2013.01); *A61L 2202/11* (2013.01); *A61L 2202/14* (2013.01)
(58) Field of Classification Search
CPC . A61L 2/0047; A61L 2202/11; A61L 2202/14
See application file for complete search history.

(56) References Cited

U.S. PATENT DOCUMENTS

| | | | |
|---|---|---|---|
| 6,213,619 B1 | 4/2001 | Yu | |
| 9,322,544 B2 * | 4/2016 | Carriere | A44C 15/0015 |
| 9,752,762 B1 * | 9/2017 | Poe, III | A44C 5/0007 |
| 10,344,924 B1 * | 7/2019 | Ganahl | F21V 15/04 |
| 2006/0170908 A1 | 8/2006 | Glimm | |
| 2016/0129279 A1 * | 5/2016 | Ferolito | A61N 5/0616 607/94 |
| 2017/0164878 A1 | 6/2017 | Connor | |
| 2018/0042513 A1 | 2/2018 | Connor | |
| 2019/0099613 A1 | 4/2019 | Estes et al. | |
| 2019/0262485 A1 | 8/2019 | Holdings | |
| 2022/0288253 A1 * | 9/2022 | Yahnke | F21V 33/0064 |

* cited by examiner

*Primary Examiner* — Sean M Luck
(74) *Attorney, Agent, or Firm* — Invention To Patent Services; Alex Hobson

(57) ABSTRACT

A field of reach ultraviolet light disinfecting system includes a wrist band having two or more UV light emitters to produce a shower of UV light over the hand to disinfect pathogens that may be located on the hand and/or objects and surfaces in the light field of light dispersion the UV light emitters. A field of reach ultraviolet light disinfecting device has a top-hand UV light emitter configured on the wrist band to produce a top-hand UV light field that is emitted down over the top or back of a hand, when donned on a person's wrist. A field of reach ultraviolet light disinfecting device has a palm-hand UV light emitter that produces a palm-hand UV light field over the palm of a hand. A visible light emitter may project a visible light that overlaps the UV light field to indicate the location of the UV light emission.

20 Claims, 6 Drawing Sheets

FIELD OF REACH ULTRAVIOLET LIGHT DISINFECTING SYSTEM

CROSS REFERENCE TO RELATED APPLICATIONS

The application is a national stage application of international application No. PCT/US2021/031126, filed on May 6, 2021, which claims the benefit of priority to U.S. provisional patent application No. 63/020,936, filed on May 6, 2020; the entirety of both applications are hereby incorporated by reference herein.

BACKGROUND OF THE INVENTION

Field of the Invention

The invention relates to a field of reach Ultraviolet (UV) light disinfecting device that produces a field of UV light above and below a hand to disinfect objects and surfaces before and when they are touched.

Background

Pathogens such as viruses, bacteria, and fungi are often transmitted by touching an infected surface or object that contaminate the person's hand, which can then infect the person if they touch their mouth, nose, eyes, an open wound, or other anatomical orifice. The world pandemic caused by the virus COVID-19 is attributed to the spread of the pathogen through airborne water droplets and by surface transmission and the transfer process as described. To prevent the spread of pathogens, people are encouraged to regularly and thoroughly wash their hands to remove or destroy pathogens therefrom. The use of disinfecting chemicals is another means to control infectious diseases. However, this can lead to dry skin, cracking, and painful skin conditions.

UV light has been shown to be an effective disinfecting agent in preventing and controlling infectious diseases. Disinfection is an operationally defined term that requires the agent to destroy or neutralize a statistical 99.9% of pathogens on a surface or airborne based on exposure of the pathogen to UV light in this case. Numerous studies demonstrate that UV light in a certain range is highly effective in attaining a 99.9% disinfection rate, which is based on the power of the UV source (amount of UV photons emitted), the wavelength of the UV source, the proximity and dispersion of the UV light to the pathogens, the amount of exposure time, and the combination of these variables that yields a "rate constant" for lethality that is specific to each pathogen.

UV light is absorbed by molecular bonds typically in the genetic structures of the pathogen that either alter the structure, which is called neutralizing, or the UV destroys the pathogen by breaking the molecular bond, both of which render the pathogen non-infectious. In order for UV light to be effective, it must be exposed to a surface for a period of about one tenth of a second or less based on the rate constant variables. Hence, if a person uses more than one UV light source that uses two different wavelengths of UV light that provides an effective coverage of the surface, such a system is highly likely to achieve a statistical 99.9% disinfection when the UV light is directed to the surface, even for a relatively short period of time. An added benefit is that the air between the UV source and the surface is disinfected as well. However, UV light only disinfects surfaces that receive direct exposure, so under and side surfaces that do not receive direct UV exposure will not be disinfected. Hence, the most effective disinfection occurs when a user can manipulate the surface and objects in order to ensure all surfaces are covered and this requires a hands-free situation, which this invention provides.

There are numerous UV light systems used for disinfection by individuals in the market, but they are usually hand-held and wand-like and only use one UV wavelength source. These personal disinfection systems often do not provide adequate coverage on the surface of objects, they provide no protection to the user's hand, and objects cannot be manipulated by the user's hand since they are holding the UV device. When a user can perform tasks with their hand such as manipulating an object so all sides are exposed, the disinfection process is much more effective and the use of two effective UV wavelengths adds a level of redundancy that also yields more effective disinfection. This is because one UV wavelength is typically absorbed more readily by certain molecular structures in the pathogen than another wavelength.

Therefore, employing two UV wavelengths increases the opportunities for the pathogen to be neutralized or destroyed in a very short period of time when the pathogen is exposed. This is because different vulnerable parts of its molecular structure are simultaneously targeted. In fact, absorption and molecular change at the bond is nearly instantaneous when it occurs from a single UV light photon. Increasing the time of exposure ensures that all pathogens within the dispersion zone of the UV light receive a lethal neutralizing and/or destroying dose. Note that "disinfection" is the correct term and should not be confused with the term "sterilization" that occurs when 100% of pathogens are destroyed, which happens only under very stringent conditions and only lasts for a short period of time once the sterilized objects are exposed to air All energy occurs on what is called the "Electromagnetic Spectrum", which is defined by the wavelength of the energy unit from very large (meters) to very small (Angstroms). Within this spectrum there are the light ranges of Infrared (wavelengths above 700 nanometers (nm) in size), visible light (700-400 nm), and Ultraviolet light (400-100 nm). Units of energy in these light ranges are called photons. The shorter the wavelength, the higher the energy within the photon. Hence, UV light is much more powerful than visible light and thus can bend or break molecular bonds when absorbed. Life on Earth evolved based on these energy ranges and their abundance on the earth's surface, as the source of these energies is the sun, and the atmosphere absorbs some wavelengths that can be harmful such as UV light.

UV light is generally broken down into three bands based on the nanometer wavelength. UVA occurs at 400-320 nm, UVB occurs at 320-280 nm, and UVC occurs at 280-200 nm. UV light from 200-100 nm is absorbed instantly in the atmosphere so it is not relevant to discuss further. Below UV are gamma and x-rays that are well known for their ability to be harmful and damaging to life in general if exposed in anything other than very low doses. UVA and UVB light penetrate the Earth's atmosphere and are abundant on the surface. These rays are beneficial for the synthesis of Vitamins A and D in organisms, but in higher doses these light rays are harmful and can cause erythema (sunburn) and skin cancers.

The term "Germicidal Irradiation" is given to those UV wavelengths that are effective at disinfecting pathogens. UVA is not germicidal, UVB is somewhat germicidal, but not at levels that readily achieve the goal of 99.9% disinfection, and UVC light at 200-280 nm is defined as the Ultraviolet Germicidal Irradiation (UVGI) range. In this invention, only UVGI emitting sources are being used. Hence, the general term of UV used in this application is referring to UVGI light. UVGI light can come from numerous sources, but this invention will only be using Light Emitting Diodes (LEDs) that are defined by the dominant wavelength they emit. Many UV LEDs in the market are tunable and generally have narrow band ranges. Research has shown that for the broad range of UVGI light, LEDs with dominant emittances in the range of about 250-280 nm and about 210-230 nm are most effective for disinfection.

Research has also shown that the 250-280 nm range is most effective for "destroying" pathogens by breaking molecular bonds such that scientists have been able to identify the specific bonds in given pathogens that are most vulnerable (more easily absorb the UV light leading to its alteration). The UVGI in the range of 210-230 nm is interesting, especially at the narrow range of about 222 nm where the resonant energy is readily absorbed by specific molecular bonds, but these bonds are typically "conformed" or changed in shape and not broken so that the DNA/RNA/protein structure is "neutralized" and no longer effective at its function, which for pathogens such as viruses is replication within the cells of infected individuals. The narrow range 222 nm light has also been shown to be unique in that it generally does not penetrate the skin on humans below the epidermal surface where only dead skin occurs, and the 222 nm light does not penetrate the external surface of the eyes as well. In effect, the 222 nm narrow band LEDs are recognized as being relatively safe for users.

In this invention, the system will use a destroying UV LED in the range of 250-280 nm or around 265 nm +/−15 nm. A neutralizing and potentially safe UV LED in the range of about 222 nm +/−5 nm. The use of two UV wavelengths will significantly increase the likelihood of reaching the disinfection goal of 99.9% effectiveness. This will also allow the user to control the UV light so that one, the other, or both UV lights are emitting, which improves the safety and effectiveness of the system for the user and anyone who may be near the user during operation of the system. These features and functions are explained in more detail in the Summary of the Invention and in the figures and claims that follow. In effect, this invention is a type of UV Personal Protective Equipment (PPE) that provides an "active" disinfection; whereas face shields, masks, and gloves currently in use at this writing only provide "passive" protection to users that block pathogen exposure to some degree.

SUMMARY OF THE INVENTION

The invention is directed to a field of reach ultraviolet light disinfecting device that includes a wrist band having two or more UV light emitters to produce a shower of UV light over and around the hand. This device disinfects any pathogens that may be located on the hand and it disinfects objects and surfaces in the field of dispersion of the UV light emitters. In an exemplary embodiment, a field of reach ultraviolet light disinfecting device has a top-hand UV light emitter configured on the wrist band to produce a top-hand UV light field that is emitted down over the top or back of a hand when donned on a person's wrist. In an exemplary embodiment, a field of reach ultraviolet light disinfecting device has a palm-hand UV light emitter configured on the wrist band to produce a palm-hand UV light field that is emitted down over the palm of a hand, when donned on a person's wrist. A UV light field is the dispersion of UV light emitted from the UV light emitter which is typically in a cone shape. A UV light emitter may comprise a plurality of individual UV light emitters that are arrange to provide effective dispersion with overlapping light fields from each of the individual emitters. For example, three light emitters may be arranged in a triangular configuration.

In an exemplary embodiment, the field of reach ultraviolet light disinfecting device is automatically adjustable to change the angular UV light emission as a function of the hand movement with respect to the wrist. One or more of the UV light emitters may be coupled to a deflector having an extension that extends out toward the hand to make contact with the hand. The deflector extension may be coupled to the hand by a deflector attachment, such as an adhesive. Therefore, movement of the hand will move and actuate the deflector extension and in turn actuate or pivot the UV light emitter about a pivot. The deflector extension may be directly attached to the UV light emitter or may be coupled to the UV light emitter by a linkage, such as one or more pins. In an alternative embodiment, a spring is configured to force the UV light emitters toward the hand and when the deflector extensions are deflected by movement of the hand, the UV light emitters are actuated and then return to a neutral position by the spring. In this embodiment, the deflector attachment may not be required. A pivot may be a pivot about a pivot axis, or the base of the top-hand and/or bottom-hand light base may comprise a flexible material that forms a pivot thereby enabling the light emitter to flex and pivot in and out from the wrist band.

An exemplary field of reach ultraviolet light disinfecting device may comprise a plurality of UV light emitters, wherein some of the emitters emit a skin safe or neutralizing UV light, such as UV light having a wavelength of no more than 222 nm +/−5 nm or a destroying UV light producing UV light with a wavelength of about 250 nm to 280 nm, such as 265+/−15 nm, 270 nm +/−10 nm or 270 nm +/−5 nm Gloves or other protective skin coverings may be required when the destroying UV light emitters are used. In an exemplary field of reach UV light disinfecting system, a pair of gloves may be part of the system where they may be reusable and impervious to UV light and disinfectant chemicals or disposable gloves may be used that are more sensitive to touching objects and well suited for cleaning using aerosols or liquid disinfectants while also providing safe UV light protection to the user's hands. The gloves should extend up the forearm so that the field of reach UV disinfecting apparatus is attached on the forearm close to the wrist and over the upper glove portion.

A neutralizing UV light may prevent any pathogens, such as a virus from replicating and thereby prevent infection by the virus while a destroying UV light may kill the virus or destroy it. An exemplary field of reach ultraviolet light disinfecting device may comprise a controller that enables a user to select which type of UV light they want emitted, or both UV lights may be used at the same time. In a high-risk location, such as when directly caring for an infected person or patient, a user may don gloves and switch over to a destroying UV light and when in lower risk location, such as in other areas of a hospital or healthcare facility, they may switch over to a neutralizing UV light. When only the neutralizing UV light is used, special gloves may not be required, but may be advisable if other chemical disinfectants are used or when long-term exposure of neutralizing UV light to the user's hand is anticipated as a safety measure.

An exemplary field of reach ultraviolet light disinfecting device may comprise a projected light orientation detector that may detect the hands start to move in an upward manner, wherein the projected UV light from the UV light emitters may be incident on a person's face and/or eyes. The projected light orientation detector may detect the projected light orientation or axis with respect to a horizontal axis. The controller of a field of reach ultraviolet light disinfecting device may automatically switch the UV light emitters off or to the skin safe, neutralizing UV light emitters only, thereby preventing exposure to the destroying UV light.

The controller may consist of a rotary switch to select operating modes and it may include an LED display where the status and error message may be displayed. In addition, the controller may include standardized colored lights and audio signals to indicate the status of the device. The field of reach UV disinfecting light system may be used in conjunction with other individual, active UV PPE systems that integrate the overall protection and disinfection to the user to prevent infection from pathogens. Such systems include face masks, face shields, and inline patient ventilator cartridges that disinfect air going to an infected patient and the exhausted air coming from the infected patient, which also eliminates the need for special hospital rooms that have positive airflow systems. UV disinfection cartridges may also be used in individual hospital and first responder positive pressure breathing systems to prevent pathogen infection as well. In effect, the use of active UV PPE systems will also prevent others from being infected by the user and the disinfection effects to eradicate surface and airborne pathogens may significantly reduce infection rates among other non-users. The widespread use of UV PPE may better control, manage, reduce, or prevent a pandemic situation such as COVID-19 in the future.

An exemplary field of reach UV light disinfecting system may have a detachably attachable power source such as a battery pack that is attached near the device on the forearm region or the battery pack may have a detachably attachable cable that allows the battery pack to be attached and stored away from the device on the person. A separate battery pack may be less obstructive to the user if stored or attached away from the device, the reduced weight at the forearm is desirable, and the weight distribution to another part of the user's body is an advantage, especially for relatively longer-term use of the system. The battery pack may be rechargeable and/or use replaceable batteries and it may have a status indicator so the user is aware of the remaining power.

An exemplary field of reach UV light disinfecting device may include a visible light emitter that emits a visible light, such as a white, violet or green light that is attached adjacent to the UV light emitters and has a similar light dispersion as the UV lights. The visible light may inform the user about where the UV light is being projected to and it also provides information to the user and other persons near the user to be aware of the UV light beam dispersion during disinfecting operations. If the user inadvertently directs their hand toward another person or the UV light beam is reflected off a mirror-like surface and angled toward another person, the visible light may be an effective warning to avert one's gaze, face, or exposed skin away from the UV light. If only the neutralizing UV light is used, a green visible light may signify that the relatively safe UV source is in use. If a destroying UV light is being used separately or with the neutralizing UV Light, then a visible violet light may be used to signify that greater caution for exposure is a concern.

An exemplary field of reach UV light disinfecting system may include more than one auxiliary UV light sensors so that the user may attach a sensor near another person's face or their own face as an added safety feature to avoid inadvertent exposure to any destroying UV light from the device. The auxiliary sensors may be battery operated, easily attached to a variety of objects, and it may have both an audio warning feature and visible colored lights to indicate a safe or "danger" status. The sensors and warning system on them may be highly useful when a person is disinfecting in a hospital environment near, around, or even on a patient such as their clothing or bed sheets as part of a rigorous disinfection protocol. It will inform the user and the patient and provide some level of confidence in the persons involved that the field of reach UV light system is being used safely and effectively. An auxiliary sensor may communicate wirelessly with a UV light disinfecting device and the controller coupled with the UV light disinfecting device may turn off the UV light, or provide an alert signal, such as changing the color of the visible light, activating a light alert on the wrist band, produce an audible alert or produce a vibration alert on the wrist band. The auxiliary sensor may have a wireless signal emitter and the UV light disinfecting device may have a wireless signal receiver. The wireless signal may be a short-range wireless signal, such as a Bluetooth signal and the like.

Additional safety protocols may involve the use of UV safe glasses and UV safe face shields, which may become part of the overall field of reach UV light disinfecting system. In summary, UVGI light may be used safely and effectively. Innumerable devices and behavioral protocols exist such that the user of the system may have manifold options to tailor and select the best combination of safety measures when employing the field of reach UV light disinfecting system based on the urgency, specific circumstances, and rules and regulations under which the system is used.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
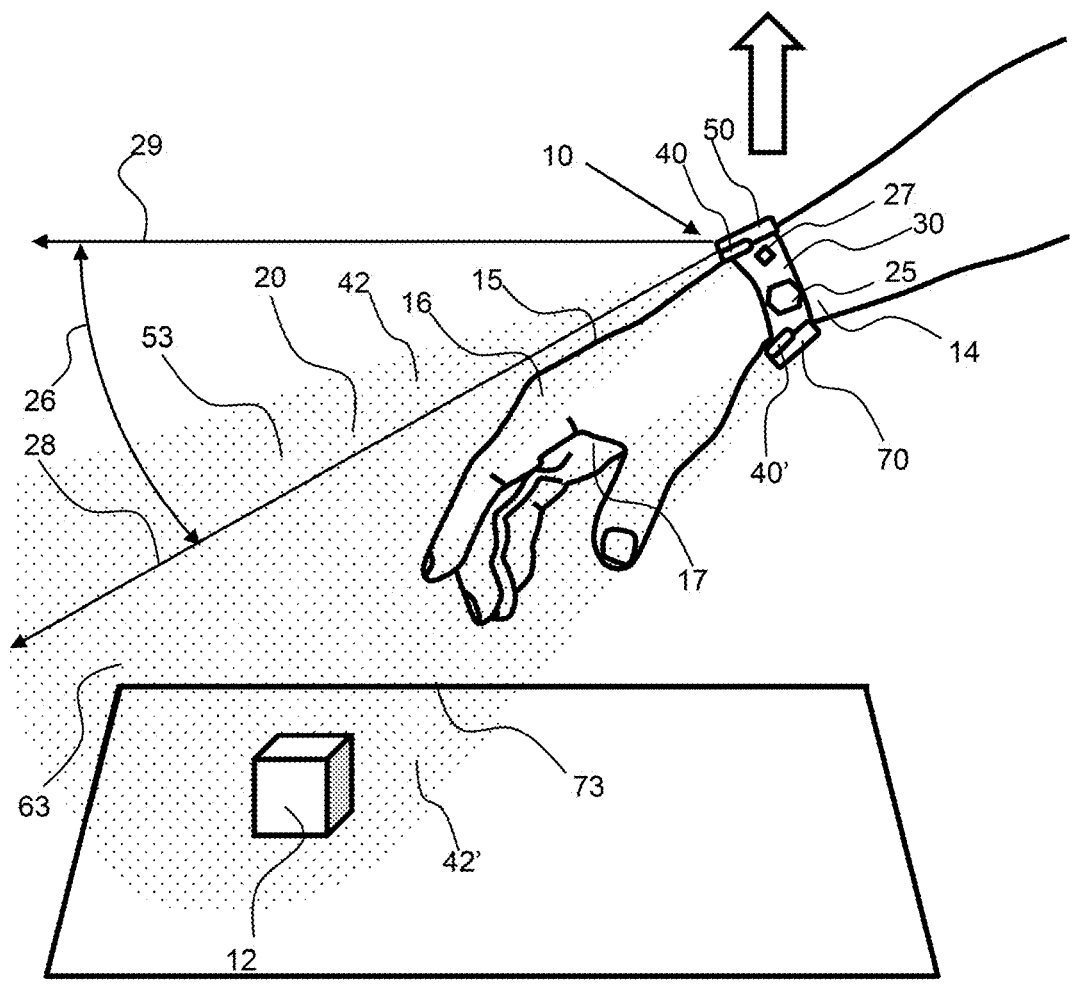
FIG. 1 shows a side view of a person reaching for an object donning an exemplary field of reach UV light disinfecting device; wherein the object is bathed in the UV light as the person reaches for it.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, a person is reaching for an object with their hand 16 and they are donning an exemplary field of reach UV light disinfecting device 10 that emits UV light 20 into their field of reach. The field of reach UV light disinfecting device has a top-hand UV light emitter 50, and a palm-hand UV light emitter 70 configured on a wrist band 30, configured around the person's wrist 14. The top-hand UV light emitter is configured on the wrist band 30 to project light down over the top-hand 15 or back portion of a person's hand and the palm-hand UV light emitter is configured on the wrist band to project light over the palm 17 of the hand. The object 12 is receiving the UV light to disinfect the object as the person reaches for it. The top-hand UV light field 53 and palm-hand UV light field 73 may overlap to form an overlap UV light field 63.

A pair of visible light emitters 40, 40' are configured on the UV light emitters 50, 70 to emit visible light 42, 42', respectively. The light emitters may be coupled with the top-hand UV light emitter 50 and palm-hand UV light emitter 70 such that they direct the visible light in a commensurate direction with the UV light. As described herein, the visible light may be white light or a colored light and the color may indicate the type of UV light being emitted, destroying versus neutralizing. For example, when neutralizing UV light is being emitted, which may be safe for skin and eye contact, the visible light may be white or green in color and when a destroying UV light is being emitted, the visible light may be violet or yellow in color.

Also shown in FIG. 1, a projected UV light detector 27 detects the orientation of UV projected light based on a person's wrist and hand orientation. As shown, the projected light orientation or axis 28 is negative or below the horizontal axis 29 having a negative projected axis offset 26 from horizontal of about 45 degrees. The controller 25 may switch from a destroying UV light, which may be damaging to skin and eyes, to a neutralizing UV light that is skin safe, when the projected UV light detector detects upward movement. Upward movement may be movement of the entire device upward, as indicated by the bold arrow, or simply angling the hand upward with respect to the wrist to change the projected light axis 28. The light deflectors may be coupled with the projected UV light detector for this purpose. An exemplary orientation detector comprises a global positioning system (GPS). The controller switch 25 turns the system on and off, and status lights, audio signals, and an LED display may be components of the controller to optimize usability and feedback to the user for more effective and efficient operation of the system.

Figure 2:
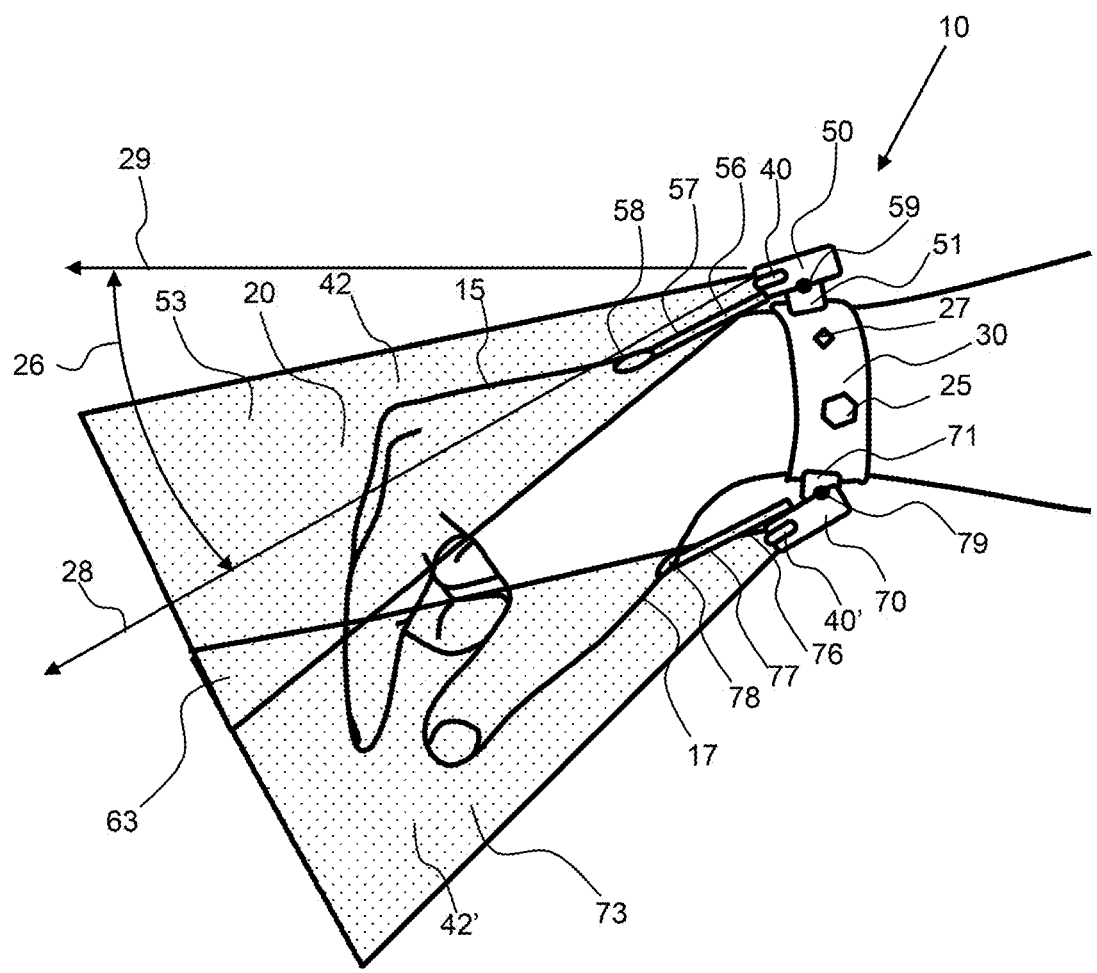
FIG. 2 shows a perspective view of exemplary field of reach UV light disinfecting device having a top-hand UV light emitter and a palm-hand UV light emitter, each having a deflector extension to pivot the UV light emitters as a function of the orientation of the hand.
Figure 3:
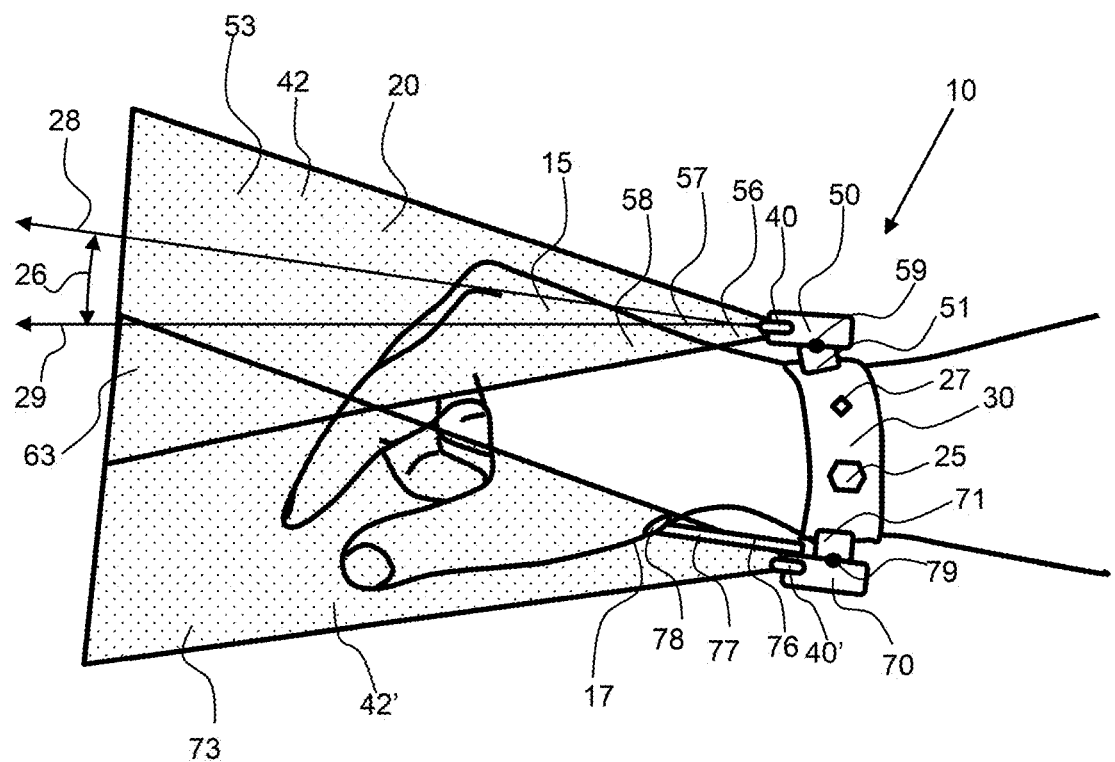
FIG. 3 shows a perspective view of an exemplary field of reach UV light disinfecting device having a top-hand UV light emitter and a palm-hand UV light emitter, each having a deflector extension to pivot the UV light emitters as a function of the orientation of the hand.

Referring now to FIGS. 2 and 3, an exemplary field of reach UV light disinfecting device 10 has a top-hand UV light emitter 50 and a palm-hand UV light emitter 70, each having a deflector extension to pivot the UV light emitters as a function of the orientation of the hand. The top-hand deflector 56 comprises a deflector extension 57 and deflector attachment 58, or portion that contacts the top-hand 15. Likewise, the palm-hand deflector 76 comprises a deflector extension 77 and deflector attachment 78, or portion that contacts the palm-hand 17. The deflector attachments may comprise an adhesive to secure the deflector attachment to the hand. The top-hand and palm-hand UV light emitters may pivot about pivots, 59, 79 respectively, as the deflectors are actuated by the motion of the hand. The pivots may be extended up away from the wrist band by a base of the top-hand UV light emitter 51, and base of the palm-hand UV light emitter 71, to allow the UV light emitters to pivot towards and away from the wrist band. As shown in FIG. 2, the top-hand and palm-hand UV light emitters are pivoted downward, as the hand is pivoted downward from the wrist and as shown in FIG. 3, the top-hand and palm-hand UV light emitters are pivoted upward, as the hand is pivoted upward from the wrist. In FIG. 2, the projected light axis 28 is below the horizontal axis 29 and therefore has a negative projected axis offset. In FIG. 3, the projected light axis 28 is above the horizontal axis 29 and therefore has a positive projected axis offset 26. The projected light detector 27 may detect this change in the projected light axis and automatically switch off any destroying UV light emitters to project no UV light or only UV light that is skin safe, such as neutralizing UV light.

Figure 4:
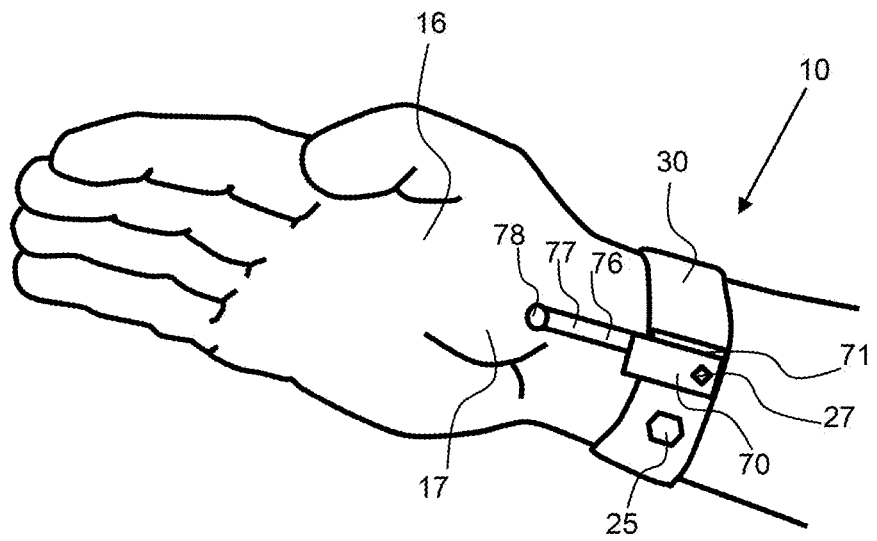
FIG. 4 shows a perspective view of a palm of a person donning an exemplary field of reach UV light disinfecting device having a palm-hand UV light emitter with a deflector extension to pivot the UV light emitters as a function of the orientation of the hand.

As shown in FIG. 4, an exemplary field of reach UV light disinfecting device 10 has a palm-hand UV light emitter 70, having a palm-hand deflector 76 to pivot the UV light emitters as a function of the orientation of the hand. The palm-hand deflector 76 has a deflector extension 77 that extends out from the palm-hand UV light emitter and a deflector attachment 78, coupling the deflector extension to the hand 16, such as to the palm of the hand 17. The deflector extension may be coupled to the light directly or through a linkage. The projected light detector 27 is configured on the palm-hand UV light emitter 70 and therefore may detect the projected light axis directly from the change of the UV light emitter orientation.

Figure 5:
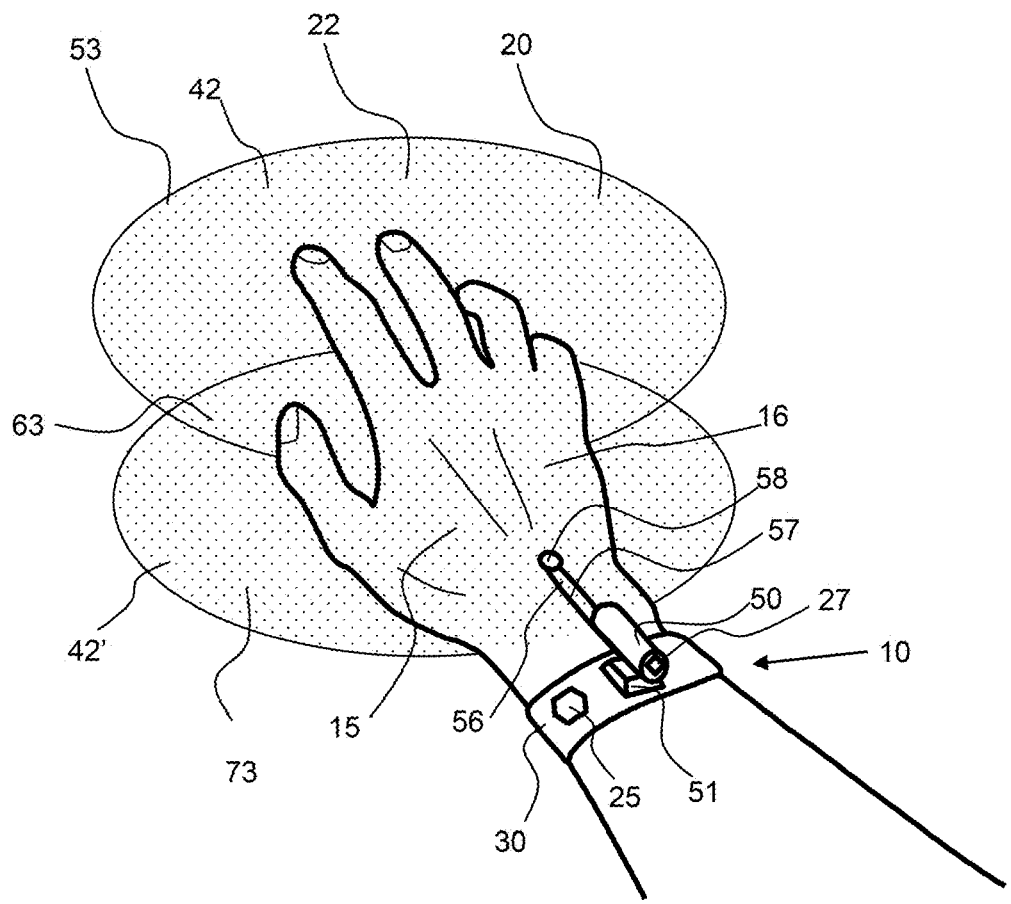
FIG. 5 shows a perspective view of a top or back of a hand of a person donning an exemplary field of reach UV light disinfecting device having a top-hand UV light emitter with a deflector extension to pivot the UV light emitters as a function of the orientation of the hand.

As shown in FIG. 5, an exemplary field of reach UV light disinfecting device 10 has a top-hand UV light emitter 50, having a top-hand deflector 56 to pivot the UV light emitters as a function of the orientation of the hand 16. The top-hand deflector 56 has a deflector extension 57 that extends out from the top-hand UV light emitter and a deflector attachment 58, coupling the deflector extension to the hand 16, such as to the top of the hand 15. The deflector extension may be coupled to the light directly or through a linkage. The UV light field 22 of UV light 20 comprises an overlap UV light field 63 the includes the overlap palm-hand UV light field 73 and the top-hand UV light field 53. The projected light detector 27 is configured on the top-hand UV light emitter 70 and therefore may detect the projected light axis directly from the change of the UV light emitter orientation.

Figure 6:
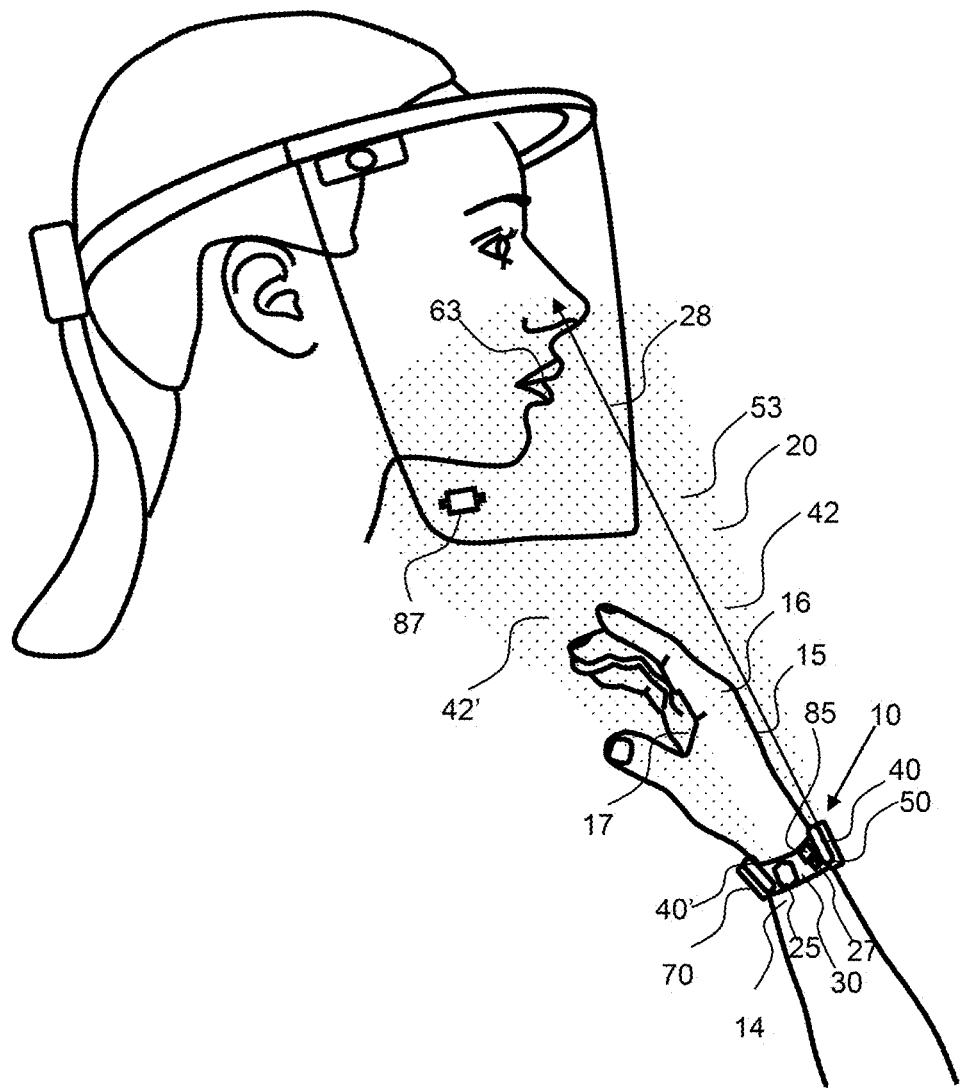
FIG. 6 shows a UV light disinfecting device aimed at a person's face and an auxiliary sensor on a face shield that is configured to detect UV light.

As shown in FIG. 6, a UV light disinfecting device 10 is aimed at a person's face and an auxiliary sensor 87 on a face shield is configured to detect UV light. The auxiliary sensor may be coupled with the UV light disinfecting device 10 through a wireless signal and the controller 25 may turn off the UV light or only the destroying UV light emitter, or alert the wearer of the UV light disinfecting device. An alert may include a change in color of the visible light emitted, wherein the color changes from white to yellow or red for example. An alert may be activated in an alert device 85 that is coupled to the wrist band 30 and may produce an audible alert via a speaker, or a vibration alert, wherein the wrist band vibrates.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A field of reach ultraviolet light disinfecting system comprising:
    a) field of reach ultraviolet light disinfecting device comprising:
        i) a wrist band;
        ii) a top-hand ultraviolet light emitter coupled to the wrist band that produces a top-hand UV light field;
        iii) a palm-hand ultraviolet light emitter coupled to the wrist band that produces palm-hand UV light field;
        wherein the palm-hand UV light field and the top-hand UV light field overlap to form an overlap UV light field;
        wherein at least one of the top-hand UV light emitter and the palm-hand UV light emitter is angularly adjustable about a pivot.

2. The field of reach ultraviolet light disinfecting system of claim 1, wherein the top-hand UV light emitter is angularly adjustable about a pivot.

3. The field of reach ultraviolet light disinfecting system of claim 2 wherein the palm-hand UV light emitter is angularly adjustable about a pivot.

4. The field of reach ultraviolet light disinfecting system of claim 1, wherein the palm-hand UV light emitter is angularly adjustable about a pivot.

5. The field of reach ultraviolet light disinfecting system of claim 1, wherein the top-hand UV light emitter is angularly adjustable about a pivot and further comprising a top-hand deflector that extends out from a coupling with the top-hand UV light emitter to contact the top of a hand, and
    wherein the top-hand UV light emitter is automatically angularly adjusted as a function of the movement of the top of the hand.

6. The field of reach ultraviolet light disinfecting system of claim 5, wherein the top-hand deflector comprises a deflector extension that extends to a deflector attachment that is detachably attached to the top of the hand UV light emitter.

7. The field of reach ultraviolet light disinfecting system of claim 1, wherein the palm-hand UV light emitter is angularly adjustable about a pivot and wherein the palm-hand UV light emitter comprises a palm-hand deflector that extends out from a coupling with the palm-hand UV light emitter to contact the palm of a hand and wherein the palm-hand UV light emitter is automatically angularly adjusted as a function of the movement of the palm of the hand.

8. The field of reach ultraviolet light disinfecting system of claim 7, wherein the palm-hand deflector comprises a deflector extension that extends to a deflector attachment that is detachably attached to the palm-hand UV light emitter.

9. The field of reach ultraviolet light disinfecting system of claim 1, wherein the top-hand ultraviolet light emitter and the palm-hand ultraviolet light emitter produce a neutralizing UV light having a wavelength of 222 nm +/−5 nm.

10. The field of reach ultraviolet light disinfecting system of claim 1, wherein the top-hand ultraviolet light emitter and the palm-hand ultraviolet light emitter produces a destroying UV light having a wavelength between 250 nm and 280 nm.

11. The field of reach ultraviolet light disinfecting system of claim 1, comprising a neutralizing top-hand ultraviolet light emitter that produces a neutralizing UV light having a wavelength of 222 nm +/−5 nm and a destroying top-hand ultraviolet light emitter that produces a destroying UV light having a wavelength between 250 nm and 280 nm.

12. The field of reach ultraviolet light disinfecting system of claim 11, comprising a neutralizing palm-hand ultraviolet light emitter that produces a neutralizing UV light having a wavelength of 222 nm +/−5 nm and a destroying palm-hand ultraviolet light emitter that produces a destroying UV light having a wavelength between 250 nm and 280 nm.

13. The field of reach ultraviolet light disinfecting system of claim 12, further comprising a controller and an auxiliary sensor configured to detect UV light and wherein the auxiliary sensor communicates via a wireless signal with the controller to turn off the destroying UV light emitters.

14. The field of reach ultraviolet light disinfecting system of claim 1, further comprising a controller and an auxiliary sensor configured to detect UV light and wherein the auxiliary sensor communicates via a wireless signal with the controller to turn off the destroying UV light emitters.

15. The field of reach ultraviolet light disinfecting system of claim 1, comprising a neutralizing palm-hand ultraviolet light emitter that produces a neutralizing UV light having a wavelength of 222 nm +/−5 nm and a destroying palm-hand ultraviolet light emitter that produces a destroying UV light having a wavelength between 250 nm and 280 nm.

16. A field of reach ultraviolet light disinfecting system comprising:
   a) field of reach ultraviolet light disinfecting device
      i) a wrist band;
      ii) a top-hand ultraviolet light emitter coupled to the wrist band that produces a top-hand UV light field;
      iii) a palm-hand ultraviolet light emitter coupled to the wrist band that produces palm-hand UV light field;
   wherein the palm-hand UV light field and the top-hand UV light field overlap to form an overlap UV light field further comprising
   b) a projected light detector that detects the orientation of a projected light axis and a controller.

17. The field of reach ultraviolet light disinfecting system of claim 16, wherein the controller automatically turns off said UV light emitters when the projected light detector detects upward movement of projected UV light, wherein upward movement of projected UV light is a change in a projected axis offset.

18. The field of reach ultraviolet light disinfecting system of claim 17, wherein the projected light detector is configured on at least one of the top-hand UV light emitter and palm-hand UV light emitter.

19. The field of reach ultraviolet light disinfecting system of claim 1, further comprising a visible light emitter that emits a visible light that at least partially overlaps the top-hand UV light field or the palm-hand UV light field.

20. The field of reach ultraviolet light disinfecting system of claim 1, further comprising a visible light emitter that emits a visible light that at least partially overlaps the top-hand UV light field and the palm-hand UV light field.

* * * * *